United States Patent
Hakalehto

(10) Patent No.: US 10,000,786 B2
(45) Date of Patent: Jun. 19, 2018

(54) METHOD AND EQUIPMENT FOR THE AUTOMATED TESTING OF MICROBIOLOGICAL SAMPLES

(76) Inventor: Eino Elias Hakalehto, Kuopio (FI)

( * ) Notice: Subject to any disclaimer, the term of this patent is extended or adjusted under 35 U.S.C. 154(b) by 728 days.

(21) Appl. No.: 13/977,327

(22) PCT Filed: Dec. 28, 2010

(86) PCT No.: PCT/FI2010/000078
§ 371 (c)(1),
(2), (4) Date: Jun. 28, 2013

(87) PCT Pub. No.: WO2012/104468
PCT Pub. Date: Aug. 9, 2012

(65) Prior Publication Data
US 2013/0302850 A1    Nov. 14, 2013

(51) Int. Cl.
*C12Q 1/04* (2006.01)
*G01N 21/00* (2006.01)
*G01N 15/06* (2006.01)
*G01N 15/14* (2006.01)
*G01N 35/02* (2006.01)
*G01N 35/00* (2006.01)
*G01N 35/10* (2006.01)

(52) U.S. Cl.
CPC ............ *C12Q 1/04* (2013.01); *G01N 15/06* (2013.01); *G01N 15/1459* (2013.01); *G01N 21/00* (2013.01); *G01N 35/00* (2013.01); *G01N 35/02* (2013.01); *G01N 35/1095* (2013.01); *G01N 2015/1493* (2013.01)

(58) Field of Classification Search
None
See application file for complete search history.

(56) References Cited

U.S. PATENT DOCUMENTS

| 5,652,143 | A | * | 7/1997 | Gombrich | B01L 3/502 422/555 |
| 5,672,484 | A | * | 9/1997 | Eden | C12Q 1/04 435/287.7 |
| 6,395,537 | B1 | | 5/2002 | Eden et al. | |
| 6,767,732 | B2 | | 7/2004 | Alocilja et al. | |
| 2010/0255529 | A1 | | 10/2010 | Cocola et al. | |

OTHER PUBLICATIONS

Hakalehto, E. et al., Fast detection of bacterial growth by using Portable Microbe Enrichment Unit (PMEU) and ChemPro 100i(R) gas sensor. Pathophysiology, Jun. 2009, vol. 16, No. 1, pp. 57-62

* cited by examiner

*Primary Examiner* — Jennifer Pitrak McDonald
*Assistant Examiner* — Qing Xu
(74) *Attorney, Agent, or Firm* — David Guerra

(57) ABSTRACT

By using the method and equipment according to this invention it is possible to analyze rapidly a large number of microbiological culture samples, or alternatively of liquid phase samples, based on the gases or gaseous compounds released by them. This invention exploits generally a sample line, along which the samples move, and it can be used for the microbial control tasks in hospitals, industry, hygiene and environmental fields. In this system gas is led into the culture vessels during the growth of the microbe, and gases released by the culture or liquids derived from them are collected into the chambers, capsules or equivalents.

14 Claims, 1 Drawing Sheet

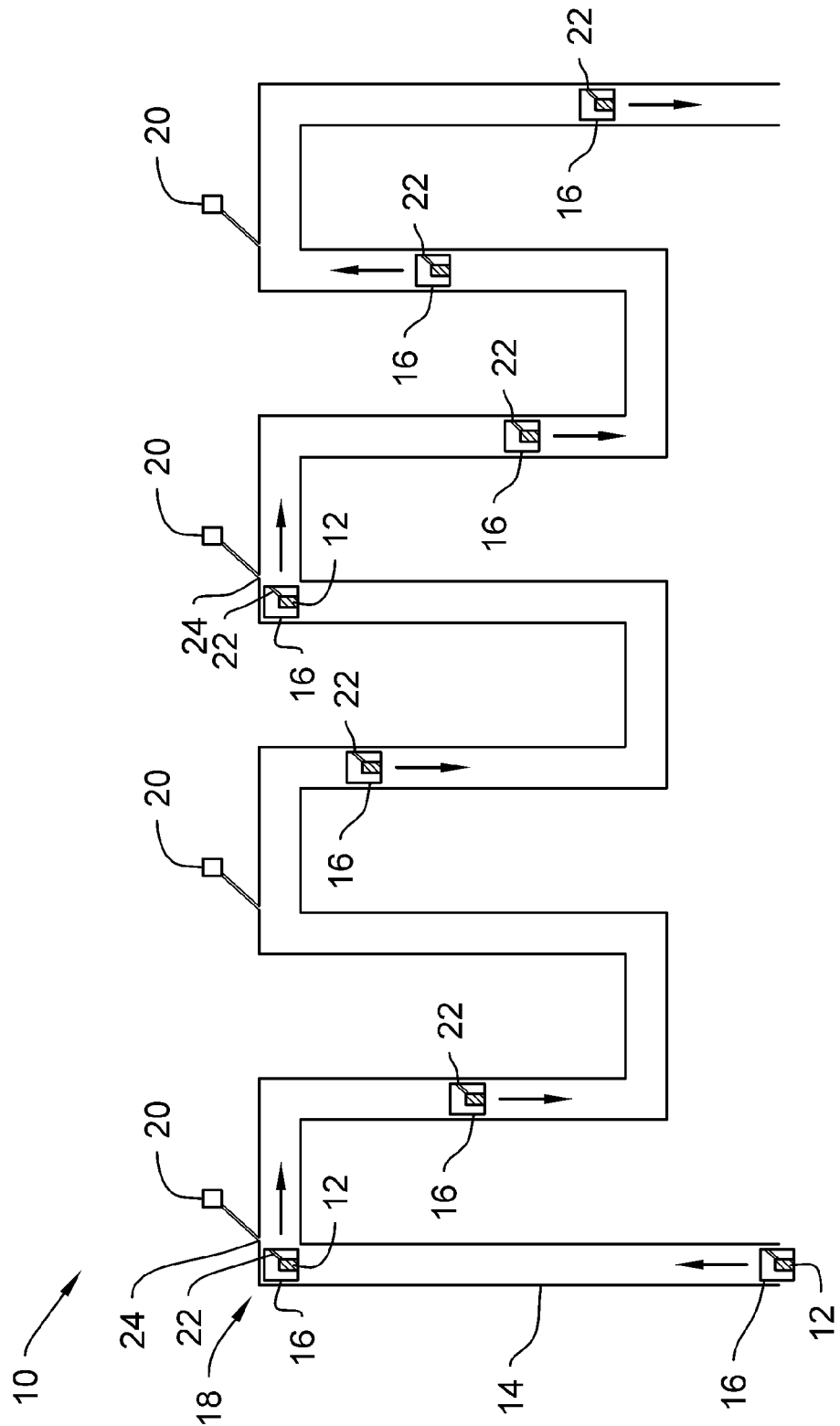

METHOD AND EQUIPMENT FOR THE AUTOMATED TESTING OF MICROBIOLOGICAL SAMPLES

CROSS-REFERENCE TO RELATED APPLICATIONS

This application is an U.S. national phase application under 35 U.S.C. § 371 based upon co-pending International Application No. PCT/FI2010/000078 filed on Dec. 28, 2010. Additionally, this U.S. national phase application claims the benefit of priority of co-pending International Application No. PCT/FI2010/000078 filed on Dec. 28, 2010. The entire disclosures of the prior applications are incorporated herein by reference. The international application was published on Aug. 9, 2012 under Publication No. WO 2012/104468 A1.

BACKGROUND OF THE INVENTION

Field of the Invention

For the use of microbiological analyses and studies carried out in hospitals and also more broadly in the field of health care, as well as in the field of food industry, industrial hygiene and environmental monitoring, there is a need for:

Description of the Prior Art 1. handling the samples as fresh and as unchanged as possible (transport, preservation and storage should be minimized);
2. getting the results rapidly, sensitively and reliably;
3. detecting as many microbes present in the samples as possible (inter alia recovery of the cells);
4. the use of enrichment culture or other culture method, which representatively reveals the microbiological characteristics of the sample;
5. the efficient handling of large number of samples.

By using the PMEU equipment (Portable Microbe Enrichment Unit), many of the needs mentioned above in steps 1-4 could be fulfilled in clinical microbiology, as well as e.g. in monitoring tasks of food industry and environmental fields. However, the need of step 5 can be satisfied especially only in large central laboratories, but then usually other objectives, like the quality and rapidity of the microbiological analyses, have to be compromised.

The PMEU equipment has been suggested for use in the hygiene culture methods in hospitals (Hakalehto, 2006), for detecting aerobic and anaerobic pathogenic bacteria (Hakalehto et al., 2007), for the research of the function and development of the intestinal microbial flora (Hakalehto et al., 2008), as well as for the detection of bacteria, present e.g. in blood or urine, at record speed based on the gases formed by them (Hakalehto et al., 2009). In the latter study the growth of *Escherichia coli* has been characterized. Also in the same studies *Staphylococcus aureus* and other *Staphylococcus, Streptococcus* and *Klebsiella* species have been detected by using the PMEU equipment together with a gas sensor. In that case microbes have been detected even from low concentrations in less than 5 hours, which is unprecedented. However, these studies have been carried out in conditions, which include a limited number of samples, but not with a large number of samples arriving continuously. This is however often the situation in hospitals, large laboratories or in other control tasks in food industry or environmental or other industrial fields. For example, in large Finnish hospitals approximately 50% of the microbiological studies could be related to the analysis of urine samples, and the large number of these samples exposes the laboratory system, even though it is a conventional automatic or semi-automatic system, to a severe stress, whereby the functional capacity and performance of the system could turn out to be limited and inadequate. As another type of samples, in which the large-scale and sufficiently sensitive and efficient analysis automatically meets practical problems, samples from blood cultures could be mentioned. For example, during generalized infection the amount of bacteria in the system of the patient could anyhow be moderately low; however, they should still be analysed as soon as possible. Prolonged analysis delays the commencement or confirmation of the appropriate treatment, and also consumes resources and produce costs. Guidelines for how to analyse gaseous emittable compounds from blood cultures have been reported (Hakalehto et al., 2009). However, this system is not automatic and does not enable the analysis of a very large number of samples at a time.

If in these above mentioned studies a detection of the gases released by the microbial culture is exploited as a basis of the measurement, an efficient and practical automated sample analysis and corresponding sensor equipment is needed. The sample collection is often decentralized, whereby means and equipment are needed for the data transfer, e.g. with respect to the changes in the cultures and gas analysis results. Recording of this information is also often useful for the purpose of later comparative analyses. In practice it is possible to analyse the function of bacteria and other microbes in the samples not only by analysing the emitted gases, but also by measuring the transmittance of infra-red radiation or light or UV radiation, or by measuring the fluorescence caused by them from the liquid growth medium (Hakalehto, 2010).

The automated microbiological analysers can of course be studied, developed and used besides in the health care and associated medical research sector and in the patient studies, also in all other fields, where there is a need to analyse accurately, rapidly and reliably large numbers of microbiological samples. These fields could include the monitoring of the equipment, processes and, hygiene in food industry, pharmaceutical and drug industry, cosmetic and process industry, the monitoring of microbiota in environmental and primary production, veterinary therapy and different ecological studies of microbes. Essential for the success of the studies and analyses is, that the capacity of the system is sufficient with respect to the number of the samples to be analysed and the rapidity of the analyses, whereby it becomes preferred to move the samples along sample lines; these type of approaches have been introduced e.g. in clinical chemistry applications. Corresponding applications in microbiological cases require the use of liquid cultures. This causes problems, if one uses conventional means to quantify microbes based on their colony growth seen on solid growth media. However, in recent studies it has been shown, that liquid cultures in the PMEU equipment could give better estimates, when the growth is monitored as described above, compared to the calculation of colony numbers on Petri dishes or on other equivalent flat-type growth media (Pesola et al., 2009).

In the PMEU equipment the beginning of the growth could reflect the original concentration of bacteria in the sample (Hakalehto 2010, Wirtanen & Salo 2010). However, the reliability of this "inverse correlation" suffers from the fact, that one does not exactly know the length of the period before the growth starts ("lag period"). For this reason it is preferred to study the growth in compartments, which locate in a chamber around the culture syringe, which compartments contain samples collected from different time points, and/or on different growth media for the subculturing and for their monitoring. At the same time one can also define more closely the quantification results of the original bacterial concentration by comparing the results obtained from different subcultures. In this case it can be assumed, that the inoculum made from the fresh culture in the syringe starts to grow without a lag period. Thus, by measuring the time needed for the appearance of the growth in the time series of the inoculated culture chambers, one can deduce and calculate the original microbe concentration from the sample taken from the culture syringe. The said time depends of course e.g. on the detection limit of the sensor used.

In fact the quantification can be done with sufficiently sensitive optical or equivalent measuring methods by calculating the number of microcolonies formed in liquid growth medium. This becomes possible, if the sensors or equivalents can be prepared sensitive enough to register microscopical optical phenomena associated with the growth of microbial particle sizes.

SUMMARY OF THE INVENTION

To attain this, the present invention essentially comprises a method for studying microbiological samples, wherein a large number of samples, for example patient samples, are studied for the detection and characterization of the microbes present in them. A gas or gas mixture, appropriate for the cultivation of the microbe, is led into the microbial cultures, and are cultivated in culture vessels. The culture vessels are surrounded by a capsule or jacket or cover or module or other equivalent shield, and that liquids, suspensions, gases or vapors or volatile compounds released by and/or derived from them are collected into compartments, chambers or equivalents, which are located in the chamber.

The method for detecting and characterization of microbes includes the moving of the microbial cultures or liquid or gaseous samples or vaporizable or volatile compounds collected from them along sample lines.

The microbial cultures to be studied are bubbled with a gas, which can be anaerobic or can include oxygen at different concentrations.

The culture vessels and/or samples move inside a tube, in which the temperature of the air surrounding them can be adjusted.

The invention may also include the step of the gas led into microbial cultures in the culture vessels is derived from the channel present in the framework of the sample line and/or temperature-controlled tube, e.g. by the aid of overpressure present in the channel.

There are, of course, additional features of the invention that will be described hereinafter and which will form the subject matter of the claims attached.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved method and equipment for automated testing of microbiological samples that has all of the advantages of the prior art and none of the disadvantages.

Still another object of the present invention is to provide a new method and equipment for automated testing of microbiological samples that provides in the apparatuses and methods of the prior art some of the advantages thereof, while simultaneously overcoming some of the disadvantages normally associated therewith.

Even still another object of the present invention is to provide a method and equipment for automated testing of microbiological samples for the use of microbiological analysis and studies carried out in the field of health care.

Lastly, it is an object of the present invention to provide new and improved equipment for performing the method in that the samples are transferred from a syringe by moving its piston into a capsule surrounding the sample cylinder, or via the capsule to the external measuring equipment for the measuring purposes. Wherein, by pushing the piston the sample transfers through the orifice of the syringe into the interior of the chamber or to the externally located sensor.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated embodiments of the invention.

BRIEF DESCRIPTION OF THE DRAWINGS

FIG. 1 is a cross-sectional view of an embodiment of the method and equipment for automated testing of microbiological samples constructed in accordance with the principles of the present invention.

DESCRIPTION OF THE INVENTION

By using the method and equipment according to this invention several samples and corresponding microbial cultures could be analyzed in a continuous mode. An example of one embodiment of the equipment 10 according to the invention is shown in FIG. 1. This invention 10 is characterized in that culture vessels 12 are moving along the sample line 14 so, that the culture vessels 12 are placed inside the capsules 16, which collect the gases formed and released by the microbes present in them. In this application the gases released, from the microbial cultures can also mean compounds vaporized or volatilized from the cultures, like VOC components (Volatile Organic Compounds). In gas analysis points or gas analysis level 18 these gases are measured e.g. by the sensor system 20 according to the reference Hakalehto et al., 2009. In this case the gas to be analyzed is discharged from the capsule or chamber 16, when an orifice 22 present in the chamber or capsule 16 becomes confronted with an orifice 24 of the analysis point 18. Then the gas is carried to the sensor 20. This sensor 20 is coupled to the automated control unit of the sample line so, that the measuring time of the gas carried to the sensor or equivalent will be appropriate.

By using the method and equipment according to this invention microbial samples can be processed in different ways and conveniently transferred forward in analysis series. The object is to seamlessly combine microbiological culturing techniques on the one hand to molecular biology methods needed and on the other hand to different sensors, which can give real-time information concerning the status of the microbial culture. Essential part of the equipment includes a culture vessel for the microbes, a sample cylinder, one preferred embodiment of which is an injection syringe, which serves as said cylinder or culture vessel.

In the culture vessel, which preferably is, as said, cylindrical and injection syringe-like, the amount of the liquid and the volume of the gas space can be adjusted by moving the piston present in the cylinder. In this way the liquid or gas can be led out from the cylinder through the syringe-like orifice located on the tip of it, or through the orifices made in its flanks. This makes it possible to construct around the syringe or equivalent cylinder chambers, cuvettes and measuring spaces, to which the gas, liquid or suspension to be analysed can be taken from the culture. These separate spaces or compartments can be prepared inside the capsule, which surrounds the syringe moving along the sample line.

The preferred gas needed for the bubbling of the culture can be conveyed into the cylinder through the syringe-like tip, like in one embodiment of the PMEU equipment (Hakalehto, 2010), or by the piston or through the walls of the cylinder. Correspondingly, the partial (sampling) or total emptying of the cylinder can be carried out, besides through the tip, alternatively by using e.g. the outlets present in its flanks, which can be prepared so, that they will be opened or closed, when the piston is moved back and forth. In this way different studies related to the characteristics of the culture cultivated or incubated in the growth syringe (culture syringe) can be carried out, also during its movement along the sample lines. Measurement or study devices needed can be placed in the capsule, or assemblies can be connected to them via the capsule, and in that way samples and subsamples can be delivered, if necessary, for additional analyses. This principle allows the collection of samples to different tests during the cultivation, and the handling of a large number of samples is enabled due to the fact, that the cylinders and capsules surrounding them move along the sample lines, if necessary, to separate measuring points, which at the same time reflect the time taken by the growth process and other transformations happened in the population.

The sampling channels can be reclosed by moving the piston so, that the orifices or assemblies or channels to the capsule or through it will be closed. Then both these sample transfer channels and the compartments or equivalents needed for their analysis can be rinsed and/or washed, if necessary, for the new run. For this purpose the capsules and/or sample line can be equipped with accessories needed for this purification process. When the capsules and cylinders located in them contain several sampling points, many different variables could be analysed from the cultures at the same time. Correspondingly, phenomena and changes at different time points, which are preferably physically separated to different sites in the sample line, can be studied.

The syringe containing the sample can be disposable, but the capsule needed for its transport, and for sampling and for analysing, can be reusable. Part of the capsule functions can be placed into the piston part or equivalent part of the syringe. This location can contain sensors e.g. for the temperature or pH of the growth medium or equivalent. By using different more specific measurement modes placed in the equipment according to the invention, several microbes and subpopulations of different types could be studied from the same culture. For this purpose, growth media of different types can be added in the chambers or compartments or equivalents placed around the cylinder, which media could be solid ones, semi-solid ones, gels or liquids. Samples for subculturing can be taken into these compartments or chambers or equivalents at different sites in the sample line, by the aid of which one can follow the development of the microbiota in the sample. The chambers meant for the subculturing can be placed e.g. annularly, whereby subcultures can be prepared on different media at the same time through several orifices, or alternatively sampling can be done as a function of time. These sampling strategies can naturally be combined in many ways so, that the samples are preferably moving along the sample line and through different measuring points. For the purpose of sampling and different measurements the syringes can also be rotated, besides getting assemblies, orifices or channels opened for the sampling and analysis purposes by moving the piston.

The capsules or chambers or equivalents can be moved along the sample line mechanically, by electrical control, magnetically, with the aid of pressurized air, or by other practical means. When they and the cultures in culture vessels included by them, move forward, places for new samples will be released. During the samples move forward, they will, like in the PMEU equipment, go through the microbial growth and/or enrichment by the aid of appropriate gas stream led into the liquid. This gas could be aerobic, microaerobic or anaerobic (free from oxygen). It spreads into the culture from the wall of the vessel at its attachment site to the sample line, and it causes bubbling, whereby the diffusion of the compounds and gases in the culture is enhanced. At the same time gases formed by the microbes will be collected into the gas stream, which is accumulated into the capsule or chamber, when it moves forward along the sample line, and is released at appropriate sites for measurement. Alternatively, the capsules and chambers, microbial cultures to be analysed located in or associated with them, can also be totally or partially stationary. Essential is, that the gas led into the microbial culture takes along volatile organic compounds (VOC) necessary for the detection of microbes, which are released from them or which are formed as a result of their function. The gas released from the culture vessels can also be collected into the chamber or capsule or equivalent, while it is moving to the next measuring point.

Microbiological samples can be clinical samples, which have been collected into test tube, sample vial or sampling syringe. The samples can be surface samples, blood, urine or fecal samples, or many other types of clinical microbial samples. The microbes present in them can be e.g. facultative anaerobes, like coliforms, *Streptococcus, Staphylococcus, Salmonella, Campylobacterium, Clostridium, Bacillus* species or any of the several other clinically important bacteria. In the method according to this invention it is essential, that gas, which is appropriate for culturing of the microbe (or bacterium) to be studied, is preferably led into the culture vessel, which is in motion. The culture vessels and equivalent chambers or capsules of different samples will move to the measurement points. This movement happens preferably in a tube, the temperature of which is set appropriate for the microbe. Said temperature, as well as the temperature, composition and pressure of the gas led into the culture, can be changed, if necessary. In the said tubular structure, where the samples move attached to the framework of the sample line, the gas can be led into the culture vessels e.g. by using overpressure. Then, after this gas has bubbled, the growth medium in the culture vessel, it will be collected into the chamber or capsule. Inside this chamber or capsule or associated with it, there could be a baggy structure, which fills up with the gas and thus collects it. This baggy structure can be emptied at the measuring point and/or at the time of measurement.

Besides in clinical analytic field, the analysis of large number of samples is also important in food industry, pharmaceutical and chemical industry, forest industry, environmental and safety oversight. Emergency cases, in which the method according to the present invention is also needed, are e.g. crises, epidemics, wars, natural catastrophes and equivalent situations. In all situations rapid and efficient microbiological analysis increases safety and lowers the costs. If the microbes to be studied are dangerous ones, the gas transferred to the sensor at the measuring point can be sterilized by filtering. When analyses from the chamber or capsule are finished, they can be purified and sterilized, if necessary.

The gas in the chambers or capsules moving along the sample line can be measured also so, that they include per se the sensors needed for the measurements, from which the measured data can be wirelessly transferred forward. At separate measuring points or levels the gas released from the chambers or capsules can be led into different analytical devices, like GC-MS apparatus (gas chromatography-mass spectometer). Correspondingly, also liquid samples can be transferred to different measuring equipments for analysis. The equipments needed for the measurement can be located also inside the capsules. To obtain appropriate culturing temperatures in the culture vessels moving along the sample line, they or the capsules containing them can be placed in a tubular structure, the temperature of which can be adjusted appropriately. When desired, filtersterilized gas can be led into the culture vessels through this tubular structure by using overpressure. The temperature and other conditions of the equipment according to the present invention can be adjusted via the control unit, which also enables the recording of the measured data or their transfer forward either with wired or wireless mode.

For the collection of the liquid or gas, the chambers/capsules constructed around or in association with the culture vessels, can be disposable or reusable. The gas led into them can be filtersterilized, if necessary. If the capsules/chambers do not surround the culture vessel, in one embodiment of the present invention one can alternatively use the method and equipment according to this invention in such way, that these chambers or capsules are moving parts, which the sample line brings to the culture vessels, from which the needed samples are collected to them for analyses. All functions of the sample line can be automatized by the control unit in all embodiments.

REFERENCES

E. Hakalehto. Semmelweis' present day follow-up: Updating bacterial sampling and enrichment in clinical hygiene, *Pathophysiology* 13 (2006) 257-267.

E. Hakalehto. Hygiene monitoring with the Portable Microbe Enrichment Unit (PMEU). 41$^{st}$ R3—Nordic Symposium. Cleanroom technology, contamination control and cleaning. Espoo, Finland, May 2010. VTT (State Research Centre of Finland), Publications 266.

E. Hakalehto, J. Pesola, L. Heitto, A. Närvänen, A. Heitto. Aerobic and anaerobic growth modes and expression of type 1 fimbriae in *Salmonella, Pathophysiology* 14 (2007): 61-69.

E. Hakalehto, T. Humppi, H. Paakkanen. Dualistic acidic and neutral glucose fermentation balance in small intestine: simulation in vitro, *Pathophysiology* 15 (2008): 211-220.

E. Hakalehto, J. Pesola, A. Heitto, B. B. Deo, K. Rissanen, U. Sankilampi, T. Humppi, H. Paakkanen. Fast detection of bacterial growth by using Portable Microbe Enrichment Unit (PMEU) and ion mobility gas sensor, *Pathophysiology* 16 (2009): 57-62.

J. Pesola, O. Vaarala, A. Heitto, E. Hakalehto. Enrichment in Portable Enrichment Unit in rapid characterization of infant intestinal enterobacterial microbiota, *Microbial Ecology in Health and Disease* 21 (2009): 203-210.

G. Wirtanen, S. Salo. PMEU-laitteen validointi koliformeilla (Validation of PMEU equipment with coliforms). Report VTT-S-01705-10 (2010), VTT Expert Services Oy, Espoo, Finland.

The invention claimed is:

1. A method of analyzing a microbiological sample for detection and characterization of microbes present in said microbiological sample, said method comprising the steps of:
   a) collecting in at least one culture vessel said microbiological sample, said microbiological sample containing at least one microbial culture;
   b) introducing a gas into said microbiological sample for cultivating a microbe in said at least one microbial culture;
   c) cultivating said at least one microbial culture in said at least one culture vessel;
   d) placing said at least one culture vessel inside a capsule so that said microbiological sample is in fluid communication with a chamber defined in said capsule;
   e) moving said capsule in a sample line, said sample line having multiple analysis sites each being located along said sample line;
   f) collecting in said chamber a released gas or liquid that is released from said at least one microbial culture;
   g) transferring said released gas or liquid from said chamber to at least one sensor associated with each of said analysis sites when said capsule is at each of said analysis sites; and
   h) measuring at least one variable concerning a status of said at least one microbial culture from said released gas or liquid using said at least one sensor, wherein said at least one sensor is associated with at least one analytical device configured to analyze the measured at least one variable.

2. The method according to claim 1, wherein said gas is introduced, in step b), into said microbiological sample by bubbling, said gas is selected from the group consisting of an anaerobic gas and oxygen.

3. The method according to claim 1 further comprising, after step e), the step of adjusting a temperature surrounding said sample line, wherein said sample line is a tube.

4. The method according to claim 1, wherein said at least one culture vessel is a syringe including a piston.

5. The method according to claim 4, wherein said capsule further comprises a device for studying said at least one microbial culture.

6. The method according to claim 4, wherein said capsule further comprises a plurality of additional chambers configured with said chamber annularly around and in fluid communication with said syringe, each of said additional chambers and said chamber having a configuration capable of receiving a portion of said microbiological sample transferred thereto and of preparing a subculture of said portion of said microbiological sample.

7. The method according to claim 6 further comprising the step of adding a growth medium to each of said additional chambers and said chamber, and introducing said portion of said microbiological sample in each of said additional chambers and said chamber so said portion of said microbiological sample is in contact with said growth medium for subculturing said portion of said microbiological sample in each of said additional chambers and said chamber.

8. The method according to claim 6, wherein said microbiological sample is transferred from said syringe to said additional chambers and said chamber by moving said piston of said syringe.

9. The method according to claim 4, wherein said syringe is disposable, and said capsule is reusable.

10. The method according to claim 4, wherein pushing said piston transfers said released gas or liquid through an orifice of said syringe into said chamber of said capsule.

11. The method according to claim 4, wherein pushing said piston transfers said released gas or liquid through an orifice of said syringe to said at least one sensor, when an orifice defined in said capsule becomes confronted with an orifice defined at each of said analysis sites of said sample line.

12. The method according to claim 1, wherein in step g) of transferring said released gas or liquid from said chamber to said at least one sensor occurs when an orifice defined in said capsule becomes confronted with an orifice defined at each of said analysis sites of said sample line.

13. The method according to claim 1, wherein said at least one sensor is selected from the group consisting of an infra-red sensor, a UV sensor, an optical sensor, a semiconductor transducer, a gas chromatography, and a mass spectrometer.

14. The method according to claim 1, wherein said analysis sites are located along said sample line to reflect a function of time taken by a growth process of said at least one microbial culture.

* * * * *